(12) United States Patent
Falkenstein

(10) Patent No.: US 10,156,555 B2
(45) Date of Patent: Dec. 18, 2018

(54) DETERMINATION OF PHYSICAL, CHEMICAL AND/OR BIOLOGICAL CHARACTERISTICS OF A LIQUID MEDIUM INTRODUCED INTO A SEALABLE CONTAINER

(71) Applicant: Steinfurth Mess-Systeme GmbH, Essen (DE)

(72) Inventor: Martin Falkenstein, Bochum (DE)

(73) Assignee: Steinfurth Mess-Systeme GmbH, Essen (DE)

( * ) Notice: Subject to any disclaimer, the term of this patent is extended or adjusted under 35 U.S.C. 154(b) by 51 days.

(21) Appl. No.: 15/022,029

(22) PCT Filed: Sep. 9, 2014

(86) PCT No.: PCT/EP2014/069217
§ 371 (c)(1),
(2) Date: Mar. 15, 2016

(87) PCT Pub. No.: WO2015/036404
PCT Pub. Date: Mar. 19, 2015

(65) Prior Publication Data
US 2016/0231301 A1  Aug. 11, 2016

(30) Foreign Application Priority Data

Sep. 15, 2013 (DE) .......................... 10 2013 015 148

(51) Int. Cl.
*G01N 1/22* (2006.01)
*G01N 33/14* (2006.01)
(Continued)

(52) U.S. Cl.
CPC .......... *G01N 33/14* (2013.01); *G01L 19/0092* (2013.01); *G01N 1/2226* (2013.01);
(Continued)

(58) Field of Classification Search
CPC ......... G01N 1/2226; G01N 2001/2229; G01N 2035/00524
See application file for complete search history.

(56) References Cited

U.S. PATENT DOCUMENTS 4,282,182 A * 8/1981 Webster .................. G01N 1/10
422/50
4,745,794 A * 5/1988 Steichen .................. G01N 7/14
73/19.03
(Continued)

FOREIGN PATENT DOCUMENTS

WO    WO 2015/036404    3/2015

OTHER PUBLICATIONS

International Search Report and the Written Opinion dated Jan. 29, 2015 From the International Searching Authority Re. Application No. PCT/EP2014/069217.
(Continued)

*Primary Examiner* — Justin Olamit

(57) ABSTRACT

The invention relates to a device and a method for determining at least one physical, chemical and/or biological characteristic of a liquid medium that has been introduced into a sealable container, said device comprising at least: one measuring head system comprising at least one pressure measuring unit for measuring the pressure of a gaseous medium and/or of the liquid medium present in the container and a temperature measuring unit for measuring the temperature of the gaseous medium and/or of the liquid medium; one movement system, at least for moving the container; and one determination system, at least for determining the physical, chemical and/or biological characteristic of the liquid medium from at least one of the individual values relating to the measured pressure and the measured temperature of the medium.

11 Claims, 2 Drawing Sheets

(51) Int. Cl.
G01L 19/00 (2006.01)
*G01N 35/00* (2006.01)
(52) U.S. Cl.
CPC ............... *G01N 2001/2229* (2013.01); *G01N 2035/00524* (2013.01)

(56) References Cited

U.S. PATENT DOCUMENTS 5,604,297 A     2/1997  Seiden et al.
7,100,427 B2 *  9/2006  Kahn .................... G01N 33/18
                                                    73/53.01

OTHER PUBLICATIONS

Angres "If It Aint Broke . . . What is Importent Measuring CO2 Content?" Brewer & Distiller International, 2 P., XP055161594, Nov. 1, 2010.
Anonymus "Automatic C02 Tester C02MS-3V-Steinfurth",XP055161590, Retrieved from Internet, Jan. 1, 2012.
Steinfurth "Steinfurth C02-Tester C02 MS", Prodduct Description, Steinfurth Mess-Systeme GmbH, XP055161592, 2. P., Jan. 1, 2012.

* cited by examiner

DETERMINATION OF PHYSICAL, CHEMICAL AND/OR BIOLOGICAL CHARACTERISTICS OF A LIQUID MEDIUM INTRODUCED INTO A SEALABLE CONTAINER

RELATED APPLICATIONS

This application is a National Phase of PCT Patent Application No. PCT/EP2014/069217 having International filing date of Sep. 9, 2014, which claims the benefit of priority of German Patent Application No. 2013 015 148.1 filed on Sep. 15, 2013. The contents of the above applications are all incorporated by reference as if fully set forth herein in their entirety.

FIELD AND BACKGROUND OF THE INVENTION

The invention relates to a device for determining at least one physical, chemical and/or biological characteristic of a liquid medium that has been introduced into a sealable container. The invention also relates to a method of determining at least one physical, chemical and/or biological characteristic of a liquid medium introduced into a sealable container.

Methods, particularly for examining the use-by date of for example foods in packaging, such as plastic packaging, are fundamentally known. Accordingly, such methods mainly relate to drinks or dairy products in the form of cheese or yoghurt, as well as meat, sweet products, spices and suchlike. By indicating a use-by date for the food, which is shown on its packaging for example, a statement can be made concerning the date by which the foodstuff in question should be consumed when properly stored with no loss or taste of quality and also without risk to health. However, a use-by date is not only shown on the packaging of relevant foods, but also the packaging of cosmetic products, which, as a rule, cannot be stored for more than approximately 2.5 years. As determining the use-by date is left to the discretion of the product manufacturer, from the relevant production series or batches individual samples are kept by means of which the quality of the entire batch or series of produced products can be proven. Such random sampling of the series or batch of products by means of individual product samples allows product manufacturers to carry out simple quality control of the manufactured product. If during product quality control a product of inadequate quality is identified, the manufacturer is able to block the entire production batch and prevent supply to the consumer.

Particularly in the drinks industry, the pressure present in the bottle as well as the material of the bottle itself, which can be made of glass, porcelain or plastic for example, are decisive for the quality and taste of the drinks themselves. For instance, particularly the carbon dioxide content ($CO_2$ content) in the drinks is an important influencing factor with regard to the taste and use-by date of the drink or food. In order to be able to determine a physical characteristic, such as the colour, the density or the viscosity, in particular of a liquid or flowable medium such as a drink, or its chemical characteristics such as the carbon dioxide content and/or its biological characteristics such as the presence of bacteria, in addition to optimum sample preparation—for which a sufficiently large amount of time is required—an appropriate measuring method is also necessary which delivers reproducible measuring results. Additionally, all packaging influences on the quality of the liquid products must also be taken into consideration. Especially in view of the continuing trend to ever newer and more cost-effective types of packaging and packaging materials for packaging the liquid media, the determination and/or measurement of the physical, chemical and/or biological characteristics of the liquid medium is incomplete without taking into account the relevant packaging influences.

SUMMARY OF THE INVENTION

One object of the present invention is therefore to at least partially overcome the previously described drawbacks. More particularly, it is the object of the invention to provide a method as well as a device for determining at least one physical, chemical and/or biological characteristic of a liquid or flowable medium which can be implemented quickly and reliably. In addition, simple operation and a low-maintenance design are desirable. Equally, the method and the device in accordance with the invention should exhibit a high level of process security and good efficiency. The present invention can also be easily integrated into already existing quality assurance systems.

The present task is solved by a device in accordance with the invention for determining at least one physical, chemical and/or biological characteristic of a liquid medium introduced into a sealable contain in accordance with the features of claim 1. At the same time, to solve this task a method with the features of present claim 11 is claimed. In the dependent device and method claims preferred further developments of the invention are set out. Features which are disclosed relating to the method in accordance with the invention also apply to the device in accordance with the invention and vice-versa. Additionally, the method in accordance with the invention can be implemented on the device in accordance with the invention.

The device in accordance with the invention for determining at least one physical, chemical and/or biological characteristic of a liquid and/or flowable medium introduced into a sealable container comprises at least one measuring head system which has at least one pressure measuring unit for measuring the medium pressure of a gaseous medium present within the container and/or of the liquid medium and one temperature measuring system for measuring a medium temperature of the gaseous medium and/or the liquid medium. Furthermore, the device in accordance with the invention comprises a movement system, at least for moving the container, and a determination system at least for determining the physical, chemical and/or biological characteristics of the liquid medium from at least one value relating to the measured medium pressure and the measured medium temperature. The pressure measuring device or pressure measuring unit of the measuring head system itself is a pressure sensor which can transform the physical parameter "pressure" and especially the absolute pressure into an electric initial parameter as a measurement of pressure. With regard to the pressure to be measure, the pressures sensors are, for example, divided into passive pressure sensors, relative pressure sensors, absolute pressure sensors or differential pressure sensors etc. The temperature measuring unit has at least one temperature sensor which is ideally arranged on or in the measuring head system. The measured temperature can also be transformed into an electrical initial parameter as a measurement thereof. Said movement system itself is, in particular, a rotary and/or pivoting movement system which can move the container along, for example, a circular path or an elliptical path, wherein, in particular it is pivoted or tilted. It is also possible for the container to be moved and/or, in particular, shaken up and down and/or back and forth along a straight movement path, i.e. in a translational direction of movement. It is also possible for the container to be rotated/pivoted about a defined axis of rotation so that at least at times and in parts the container is rotated about its own axis, which preferably extends at right angles to the longitudinal axis of the container. If the container is rotated/pivoted about a defined point of rotation or a defined axis of rotation, not only does the alignment of the container itself change, i.e. the base area of the container is at least at times and at least in parts arranged, when viewed in the vertical direction, above upper or inlet area of the container. Rather, the rotary or pivoting movement also brings about a flow of the liquid medium introduced into the container, into the mouth/opening area of the container from the base area and then back to this base area. Accordingly the container is preferably tightly closed by means of a sealing element in such a way that during a rotary or pivoting movement, as well as during a translationally aligned shaking movement, flowing out of the liquid medium is reliably prevented. In addition to the liquid medium, a gaseous medium, such as air for example, or an air-carbon dioxide mixture, is also generally present in the sealed container. Consequently, during the rotating or pivoting movement or also the shaking movement of the container the liquid medium is mixed with the gaseous medium or further gaseous medium is released from the liquid medium and mixes with the already present gaseous medium. Advantageously mixing of the media takes place until a phase equilibrium or state of balance between the gaseous medium and the liquid medium is achieved within the preferably sealed contained. A state of phase equilibrium is taken to mean a chemical balance in which the concentration or the quantity of products and educts no longer changes. In a chemical equilibrium the rates of forward and back reactions are equal. Thus, before determining the physical, chemical and/or biological characteristic of the liquid medium, i.e. before sample measurement, it is conceivable to bring the container to a predefined temperature in order to achieve a state of equilibrium.

Said liquid medium is advantageously a foodstuff, in particular drink, above all a drink containing carbon dioxide ($CO_2$).

It is also conceivable that at least before determination of the physical, chemical and/or biological characteristic of the liquid medium, at least one geometric characteristic of the container in which the medium is located is recorded in a metrological manner, in particular purely optically.

Advantageously the device in accordance with the invention is used to combine the sample preparation, that is to say the mixture of the gaseous with the liquid medium, with a measuring device for determining a physical, chemical and/or biological characteristic of the liquid medium. In this way the acquisition and also the operation of an additional device can be spared, through which not only is the processing or cycle time shortened during the determination of the characteristic of the liquid medium, but the spatial requirement in an appropriate measuring laboratory, for example, is also reduced. Furthermore, with the device in accordance with the invention and consequently through the determination of the liquid medium which is in the sealable container, the possible packaging influences on the liquid medium can also be advantageously taken into consideration when determining the characteristic. Also advantageously, unnecessary interference factors in the determination of the characteristic of the liquid medium, which could, for example, occur during the reapplication of the container from the sample preparation device onto the measuring device, can be avoided through the direct measurement of the fluid medium in the packaging with one device in accordance with the invention.

Within the context of the invention it is conceivable that the device is designed in such a way that sample preparation can be carried out simultaneously with the determination of a physical, chemical and/or biological characteristic of the liquid medium. For this, electronic slide contacts can be provided between a stationary base section or frame of the device and the measuring head system in order to transmit electrical measuring signals from the measuring unit of the measuring head system, which is moved by the movement system during sample preparation, to the stationary base section for further processing. It is also conceivable for the electrical measuring signals to be transmitted from the measuring unit of the measuring heat system via a wireless connection to the stationary base section for further processing. As a wireless connection a radio connection such as, for example, BlueTooth, NFC, ZigBee, WIMIX, WISA or other WLAN connections can be used. For this, arranged in both the measuring head system and in the base section are appropriate communication modules for the radio connection which can exchange electrical measuring signals or other data between each other.

The determination system which is advantageously used for determining and evaluating the characteristic of the liquid medium is preferably operated fully automatically or also semi-automatically.

It is also conceivable that the measuring head system has a spike for piercing an area of the wall of the container and consequently to introduce the temperature measuring unit and/or the pressure measuring unit into an interior area of the container. Advantageously an area of the closure element is pierced, particularly if the container itself is made of glass or a glass-like material. In this case the closure element can be considered as a component part of the container, which in addition to the closure element can also comprise a container wall or container body. The measuring head system itself is advantageously a movable or pivotable system which can be mounted on an opening of the receiving container which at least partially serves to receive the container. It is also conceivable that the measuring head system is mechanically connected to the movement system and is moved and/or shaken therewith along with the container. The measuring head system can be pressed from outside onto the container, more particularly the closing element, with a sealing element or sealing ring in order to securely and reliably seal the area around the spike in a pressure-tight manner.

Advantageously the temperature measuring unit extends at least in sections along the spike so that when the spike pierces an area of the closure element of the container or also a section of the wall of the container, not only the spike itself or an area of the spike itself is introduced into an interior area of the container, but at the same time also the temperature measuring unit or a section of the temperature measuring unit is introduced into the interior area of the container by way of the spike. In addition it is also conceivable that not only the temperature measuring unit, but simultaneously also the a pressure measuring unit is introduced into the interior area of the container, wherein it is also possible that the pressure measuring unit itself remains in the area of the measuring head system.

The temperature sensor which is, for example, an electric or electronic sensor which delivers an electric signal as a measure of the temperature, can for example be designed as an NTC thermistor (hot conductor) or a PTC thermistor (cold conductor) or also as an integrated semiconductor temperature sensor. It is also conceivable that in addition to the arrangement of a temperature measuring unit or a temperature sensor and the arrangement of a pressure measuring unit or a pressure sensor the device in accordance with the invention or also the measuring head system itself has further sensors, such as, for example, an optical sensor, a weight sensor, a humidity sensor, a piezo sensor, a capacitive and/or inductive sensor etc. By way of the various sensors it is therefore conceivable to detect or measure different characteristics of the liquid as well as any gaseous medium within the container. Advantageously the spike is firmly connected to a surface of the measuring head system so that in the event of a movement of the measuring head system itself onto or towards the container, the spike is also moved onto or towards the container. Hence it is possible for the spike to have a pointed distal end, more particularly a needle-like end, which is required for penetrating into the interior of the container. Due to the penetration or piercing of an area of the container or the closure element of the container by the spike, a destructive test of the container or the closure element is carried out.

The receiving container or receiving device which serves to at least in sections receive the container and can hold the container partially or wholly up to its opening or mouth area is advantageously at least in parts optically transparent or at least has an optically transparent window. Hence it is also conceivable that the receiving container holds and surrounds the container in a pressure-tight manner, wherein the receiving container advantageously has the design of the container. The container for the liquid medium is for example a bottle into which a drink, for example water or a lemonade-like drink is filled. The closure element is, for example, a screw top, a cork closure or also a crown cork closure or similar closure. Explicitly the container for the liquid medium can be a glass or plastic, more particularly a PET (polyethylene terephthalate) bottle. Plastic containers as well as PET bottles or containers have the problem that that are not pressure-tight and/or $CO_2$-tight over a longer period of time.

In accordance with an advantageous further development the measuring head system has at least one sealing element for the sealed closing of an opening of the receiving container and/or the sealing closing of an opening of the container and, in particular, the closure area. Accordingly the measuring head system in particular has sealing ring or a sealing edge, more particularly of a sealing material containing rubber which on arranging the measuring head system on the container and consequently on the receiving container is applied between the measuring head system and the opening edge of the receiving container or between the measuring head system and a surface of the closure element of the container in such a way that the emergence of a, more particularly gaseous, medium can be prevented.

It is also conceivable that on a surface of an outer side of the receiving container, the device in accordance with the invention has at least one tension element for locking the measuring head system in the area of an opening of the receiving container. Advantageously, by means of the tension element arrangement and/or locking of the measuring head system on an opening of the receiving container and/or an upper area, more particularly the mouth area and preferably the area at which the closure element is arranged, of the container. Accordingly the tension element is advantageously used for locking the measuring head system on the opening of the receiving container and consequently for clamping the container into the receiving container, that is to say between the receiving container and the measuring head system. Through this a pressing force for the sealing element between the measuring head system and the receiving container or between the measuring head system and a surface of the closure element of the container can be produced.

In accordance with another advantageous further development the temperature measuring system has a tubular insulation element made of a thermal energy insulating material, through the interior of which a thermal energy-conducting or conductive transfer element extends. Accordingly it is conceivable that the insulation element consists, in particular, of a material containing carbon or also a ceramic or also a material containing plastic, while the transfer element itself is a thread-like element, consisting of a conductive metal, such as silver, for instance. However, it would also be possible for the transfer element itself to be in the form of a groove extending along the inner side of the insulation element and coated with a thermal energy conductive material. It is also conceivable that the device in accordance with the invention has a tempering system for tempering the container and, in particular, the liquid medium in order to advantageously achieve a state of balance within the container.

In accordance with a preferred further development of the invented device, the device in accordance with the invention and/or the determination system of the device in accordance with the invention has an evaluation system for evaluating the measured values, such as the medium pressure and the medium temperature, in particular taking into account the predefined correlation values. Accordingly it is conceivable that in relation to certain types of liquid medium, i.e. in relation to particular different types of drinks, corresponding physical, chemical and/or biological characteristics of the liquid medium are stored, for example in the form of a database for different temperatures and pressures. The evaluation device of the determination system can then refer to these stored data. It is also conceivable that in addition to the evaluation unit, the determination system also has a display unit in the form of a screen, by means of which in addition to the different measured pressure and temperature values of the liquid medium or the gaseous medium, the determined characteristic value in relation to the physical, chemical and/or biological characteristic of the liquid medium can be shown. It is also conceivable for the display unit to simultaneously act as an input device, in that it is equipped with, for example, a touch-sensitive screen (touchscreen). The input device itself can, however, also be a separate unit which is connected, for example via the determination system, to the display unit. Via the input device a person is able, for example, to indicate to the determination system which type of liquid medium, i.e. in particular, what type of drink, is in the sample container in question. Entering the type of liquid medium enables the determination system and, above all, the evaluation unit to read the appropriate characterisation value from the database taking into consideration the determined temperature and determined pressure. It is also conceivable that in addition to the input device, or also as an alternative to the input device, the determination system has a scanner unit, by means of which, for example, a barcode, strip code, colour code, QR code etc. located on the container or packaging of the batch of manufactured products can be read in. Through reading in the code, the determination system and, in particular, the evaluation unit of the determination system is informed about which type of liquid medium is present in the container arranged in the device. Furthermore, it is also possible that the determination system has a memory unit in which the individually measured values, more particularly with regard to the pressure and the temperature, and/or the characteristics determined in relation thereto, especially the physical, chemical and/or biological characteristics of the liquid medium can be stored, at least for a time and preferably in the long term. Advantageously reading out of this memory unit is possible at all times. Moreover, the determination system can also comprise a receiver unit and/or a transmitter unit or a combined receiver and transmitter unit which on the one hand receives the determined or measured data relating to the pressure and the temperature and on the other hand can send the determined characteristic value of the liquid medium relating to the physical, chemical and/or biological characteristic of the liquid medium to a third, separate unit, such as a server or an external computer etc. As a result, the device in accordance with the invention is able to determine data relating to the characteristics of the liquid medium or the manufactured drink product which can be quickly and securely called up at any time and transmit these data to appropriate external evaluation units.

It is also possible for the receiving container to comprise a container insert element for the height adjustment and centring of the container within the receiving container. The container insert element is preferably a separate element made at least partially of a rigid, stiff or non-elastic material, such as a plastic. Advantageously the container insert element can also be removed from the receiving container at all times. It is therefore conceivable for the container insert element to be designed in accordance with the configuration of the individual container, so that an appropriate container insert element can be selected depending on the design of the container to be inserted into the receiving container. Consequently the container insert element has at least one depression and/or one recess and/or a projection and/or wall, by means of which the container can be arranged within the receiving container. In order to check whether the correct container insert element for the height adjustment and centring of a particular container within the receiving container has been selected, a person working in a test laboratory or on a production line who is determining and monitoring the determination of a characteristic of the liquid medium can manually check the correct height adjustment of the container in the receiving container, or this can done automatically by the device itself by means of a height gauge or a light barrier etc. For automatically checking the height adjustment and/or the centring of the container in the receiving container a light barrier can be used for example. Correct height adjustment of the container within the receiving container is particularly necessary so that on the one hand when being arranged on the receiving container the measuring head system does not destroy or damage the container, in particular its opening or mouth area, and on the other hand so that the container can be arranged between an area (base area) of the receiving container and the measuring head system with no or little movement so that during a shaking movement or rotating or pivoting movement of the container the latter does not slip within the receiving container and possible damage the measuring head system and/or the spike.

In accordance with an advantageous further development of the device in accordance with the invention, for removing the gaseous medium present in the container it has an extraction unit arranged on an outer side of the receiving container or the stationary base section of the device in accordance with the invention and at least one conduit element which extends from the removal unit to the spike. For targeted control and extraction a control valve is arranged in the area of the conduit element and can open and close it. Advantageously the extraction unit is used for removing a gaseous medium, more particularly a mixture or air and carbon dioxide, present in the container, at least, in terms of time, before starting to determine the characteristic or characteristic value of the liquid medium. The extraction unit (Snift collector) conveys the gaseous mixture either into an appropriate holding container or into the environment. The conduit element of the extraction unit for conveying the gaseous mixture from the interior of the container to outside extends from the extraction unit via, in particular, the spike into the interior of the container so that, advantageously, no second area of the container and, in particular, no further wall area of the container has to be pierced in order to allow the extraction and/or discharge of the gaseous mixture from the container.

The method in accordance with the invention for determining at least one physical, chemical and/or biological characteristic of a liquid medium introduced into a sealable container comprises at least the following stages:

continuous measuring of a medium pressure of a gaseous medium present in the container and/or of the liquid medium by way of a pressure measuring unit of a measuring head system as well as of a medium temperature of the gaseous medium and/or the liquid medium by way of a temperature measuring unit of the measuring head system during a movement of the container, detection of the establishment of a state of phase equilibrium between the gaseous and the liquid medium in the container, transferring of the measurements to a determination system in order to determine the physical, chemical and/or biological characteristic of the liquid medium from at least one value, in each case relating to the measured medium pressure and the measured medium temperature.

Advantageously the medium pressure and also the medium temperature are measured continuously, i.e. at defined time intervals or time period. Hence it is conceivable that the medium pressure and the medium temperature are measured, for example, every hundredth or tenth of a second, preferably every second or every five or every ten seconds over a defined period of time, wherein the defined period of time extends from the start of the measuring procedure up to the establishment of a state of phase equilibrium or a state of chemical equilibrium of the gaseous medium and the liquid medium present inside the container. Advantageously not only are the pressure and temperature measured simultaneously, but at the same time the container moves along, for example, a defined movement path, wherein the movement path can be a circular path or also an elliptical path. As described above, it is thus conceivable that the container, which advantageously is arranged in a receiving container and is therefore moved together with the receiving container, is either shaken along a translational path or also rotated or pivoted about a point of rotation or axis of rotation so that mixing of the gaseous medium present in the container with the liquid medium present in the container can take place. Advantageously the container rotates evenly upside down, which advantageously leads to an optimum phase equilibrium which in turn forms the basis of optimum reproducibility and measuring accuracy of the characteristic value of the liquid medium. Beneficially, with the method in accordance with the invention the method of preparing the liquid medium for determining the characteristic is connected to the method of determining the characteristic itself. This means that the method for establishing a state of phase equilibrium between the gaseous medium and the liquid medium in the container is advantageously combined with the method of measuring the medium pressure and the medium temperature and thus with the method of determining the characteristic on the basis of the determined medium temperature and the determined medium pressure. This achieves that sample preparation can be discontinued immediately on reaching the phase equilibrium, which can now be directly measured by the device in accordance with the invention. In this way the sample preparation time can be reduced to an absolute minimum. In addition, through continuous measurement during the movement of the container it is assured that phase equilibrium has been established. In phase equilibrium the measured values no longer change over time and only fluctuate insignificantly within a defined measurement range. As soon as the measurements no longer change, as described above, the optimum phase equilibrium has been reached in the container and the most recently obtained measurements can be used for determining the physical, chemical and/or biological characteristic of the liquid medium.

In the determination of the physical, chemical and/or biological characteristic of the liquid medium a carbon dioxide concentration value of the liquid medium is advantageously determined. As, in particular, the taste as well as the use-by date of a drink in a container are influenced by the magnitude of the dissolved carbon dioxide content, the device and the method in accordance with the invention are advantageously used for determining, in particular, the $CO_2$ content in, for example, wine, beer, water or soft drinks, in order to be able to ensure a uniform $CO_2$ content in the produced or bottled drinks of each production batch. The $CO_2$ concentration in the liquid medium can, in particular, be determined through pressure and temperature measurement during the establishment of a state of equilibrium between the gaseous and liquid phase. Particularly in order to determine the carbon dioxide concentration in the liquid medium, with reference to Henry's law the partial pressure of a gaseous medium present above the liquid medium is determined, wherein this partial pressure is directly proportional to the carbon dioxide concentration of the liquid medium. The Henry's law equation is thus the drinks-specific equation in accordance with which the carbon dioxide concentration in the liquid medium is determined.

Further measures and advantages of the invention are set out in the claims, the following description and the drawings. The disclosed features of the device in accordance with the invention also apply to the method in accordance with the invention and vice versa. In the drawings the invention is shown by way of one schematic example of embodiment. Features from the claims and in the description can be essential to the invention per se or in any combination.

BRIEF DESCRIPTION OF THE SEVERAL VIEWS OF THE DRAWINGS

It is shown.

DESCRIPTION OF SPECIFIC EMBODIMENTS OF THE INVENTION

Figure 1:
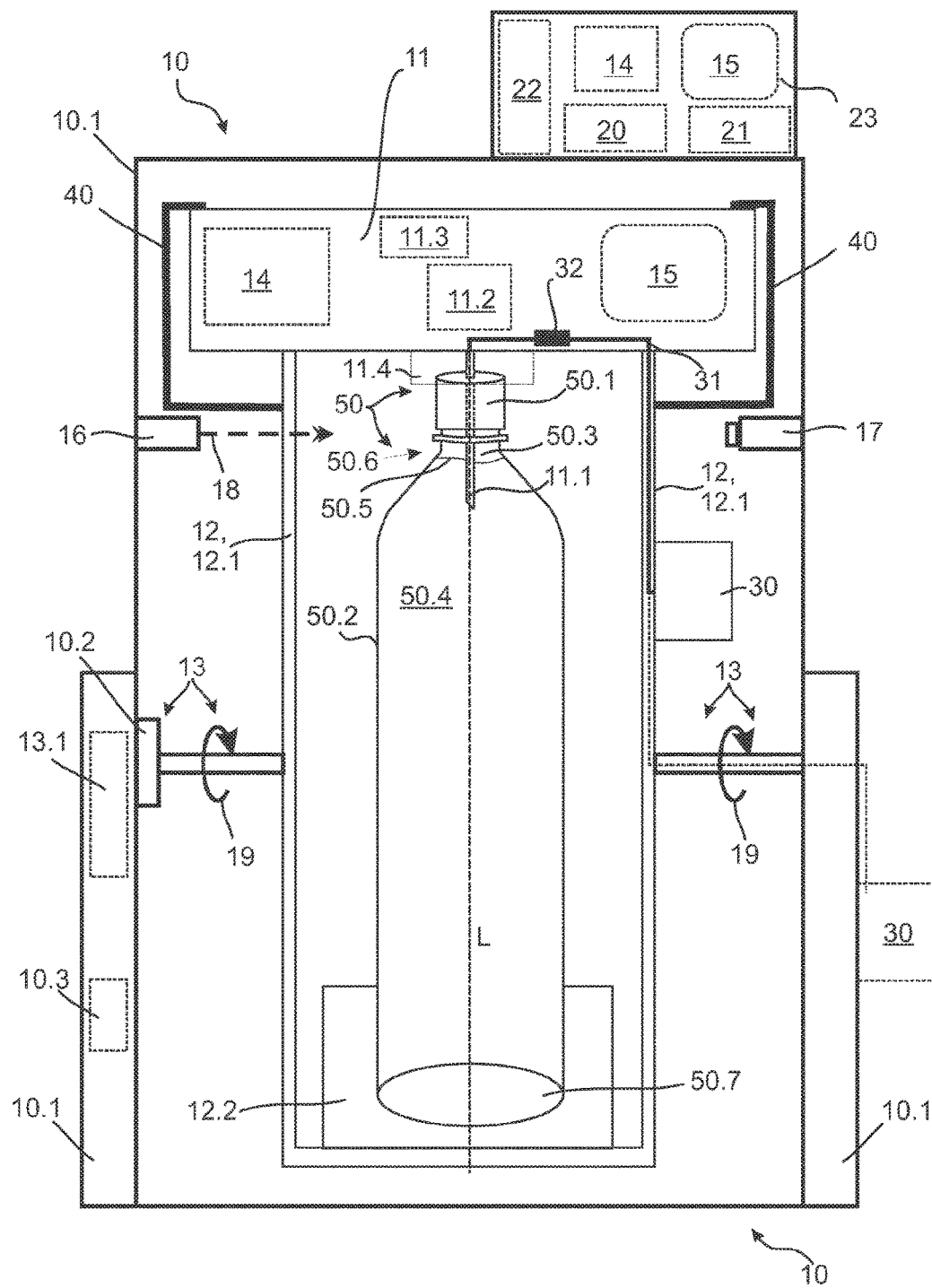
FIG. 1 shows a schematic view of a form of embodiment of the device in accordance with the invention and
FIG. 2 shows a schematic diagram of the course of a method of determining a physical, chemical and/or biological characteristic or a liquid medium.

Shown in FIG. 1 is a side view of a device 10 in accordance with the invention for determining at least one physical, chemical and/or biological characteristic of a liquid or flowable medium 50.4 introduced into a sealable container 50 which advantageously is a foodstuff and preferably a drink. The device 10 has a mechanical receiving device 12 or a mechanical receiving container 12 for receiving and arranging the container 50 on the device 10. The containers 50 are advantageously filled with the liquid medium 50.4, wherein filling of the medium takes place, for example, at a station which is not shown. The container 50 to be examined or the container 50 containing the liquid medium 50.4 to be examined is, in particular, a liquid container in the form of a bottle 50.2, more particularly a glass or plastic bottle, such as, for example, a PET bottle, which is closed with a closure element 50.1 such as a screw-top lid, a crown cork cap or a cork stopper or a comparable lid. A filling level 50.5 of the liquid medium 50.4 in the container 50.2 is also indicated schematically. Preferably the container 50.2 is filled with the liquid medium 50.4 up to neck area 50.6 or into this neck area 50.6. Above the filling level 50.5 is a head room 50.3 which is not usually filled with the liquid medium 50.4 but with a gaseous medium which usually contains carbon dioxide ($CO_2$). So that this gas cannot escape from the head room 50.3 the container 50.2 is closed with the closure element 50.1.

As can also be seen from FIG. 1, the container 50 has been pierced with piercing means 11.1 or a piercing spike 11.1 projecting, for example, through a wall of the closure element 50.1 into the liquid medium 50.4. However, in the context of the invention it is sufficient if the spike 11.1 is taken or projects through the closure element 50.1 into the head room 50.3 of the container 50.2 and therefore does not come into contact with the liquid medium 50.4 when the container 50.2 is standing upright on its container base 50.7. Advantageously the piercing spike 11.1 is itself part of the measuring head system 11 which is arranged above the closure element 50.1. In relation to this the measuring head system 11 can also be used for sealing the closure element 50.1 on piercing of this closure element 50.1 by means of the piercing spike 11.1 and for example a sealing element 11.4 indicated in a dashed manner. This indicated sealing element 11.4 is advantageously clamped or fixed in a sealing manner between the measuring head system 11 and the container 50.2, more particularly the closure element 50.1. In the measuring head system 11 which is principally assigned to the device 10 in accordance with the invention, at least one measuring unit 11.2 and, in particular, a sensor 11.2 be arranged. This measuring unit 11.2 can, in particular, be a temperature measuring unit or a temperature sensor and/or pressure measuring unit or a pressure sensor. Several measuring units 11.2 can also be provided in the measuring head system 11 which also directly record the characteristic of the liquid medium 50.4 directly through the piercing spike 11.1.

Additionally, the device 10 is fitted with a movement system 13 and, more particularly, a rotating and/or pivoting device 13 or a rotating and pivoting mechanism 13. Advantageously the movement device 13 is essentially designed in a bracket-like 12.1 manner and serves to securely hold and fix the container 50 via the receiving container 12. At the lower, distal end of the receiving container 12 a container insert element 12.2 can be arranged, which in addition to centering and height-adjusting the container 50 within the receiving container 50.2 and thereby also in the device 10 is also used for the form and/or force fitting securing of the container 50. Beneficially therefore, by means of the receiving container 12 and, in particular, its container insert element 12.2, the container 50 can be aligned or arranged geometrically precisely, i.e. centred and height-adjusted within the device 10. The measuring head system 11 which advantageously is also connected to the movement system 13 with the bracket 12.1 of the receiving container 12 and is moved therewith can also comprise an evaluation unit 14 as well as a display unit 15. However, it is also conceivable that the measuring head system 11 is connected in a data-transmitting manner to the determination system 23, e.g. through wired slide contacts 10.2 or radio-communication modules 10.3, 11.3 or wirelessly, wherein in addition to the evaluation unit 14 and the display element 15 the determination element 23 also has a memory unit 20 for storing inputted and/or recorded data and values, such as the measured pressure values and temperature values, as well as a transceiver unit 21 for receiving the measured values (pressure/temperature) from, for example, the measuring head system 11 as well as for transmitting data entered via an input device 22, such as data relating to the nature or composition of the liquid medium to be examined, the type of container 50 (glass material, plastic material etc.). It is also possible for the display unit 15 to be in a touch-sensitive screen (touchscreen) via which data/values can also be entered, so that the display unit is simultaneously an input device 23 and a separate input device 22 can be dispensed with. Data transmission between the measuring head system 11 and the determination system 23 can be in cable form via the slide contacts 10.2, or wireless via the corresponding communication modules 10.3, 11.3, for example by Bluetooth or wireless LAN. It is also conceivable that the determination system 23 is integrated with the corresponding units 14, 15, 20, 21, 22 in the measuring head system 11 and is consequently a component of the measuring head system 11. Advantageously the determination system 23 is arranged in a stationary manner on the device 10 or the base section 10.1 of the device 10 and does therefore not, as opposed to the measuring head system 11, with the receiving container 12 and the container 50 arranged therein, move about a defined point of rotation or axis of rotation, as shown by reference no. 19 for example.

It is also conceivable that the bracket 12.1 is not only arranged on a receiving container 12, which primarily, as an at least partially enclosed housing having an inlet opening, is in the form of a cylinder, and at least surrounds this receiving container 12 in sections. Instead, the bracket 12.2 can itself act as receiving means and thus largely replace the receiving container 12 so that the container insert element 12.2 is beneficially arranged directly on the bracket 12.1, in particular on its lower, distal end, in order to position, align and centre the container 50. It is also conceivable that within the receiving container 12, a previously described, but not shown here, tempering unit is arranged serving to temper the liquid medium 50.4 in order to be able to accelerate the establishment of a state of phase equilibrium within the container 50.

Furthermore, within the device 10, in particular in the area of the head room 50.3 of the container 50 at least one light source 16, e.g. in the form of a laser can be arranged, which emits a light beam 18 that shines through the container 50. The light source 16 is, in particular, aligned in such a way that the emitted light beams or electromagnetic waves essentially hit a longitudinal axis L of the container 50 at a right angle. On the side of the container 50 opposite the light source 16 an optical sensor 17 can be arranged within the device 10 which records the emitted light beam 18 by measurement. An optical sensor 17 can also be provided on the light source itself 16 for measuring a part of the reflected light beam 18 of the light source 16. Through the provided light source 16 as well as the optical sensor 17, non-destructive, indirect sample measurement of the container 50 with the liquid medium 50.4 can be carried out. Advantageously the emitted light beam 18 is not restricted to light visible to humans so that light beams 18 of other wavelengths are also conceivable.

With reference number 40 a tension element is schematically shown extending from an outer side of the receiving container 12 to an area of the measuring head system 11 and consequently preferably firmly connecting the measuring head system 11 to the receiving container 12 while also exerting a clamping force on the indicated sealing element 11.4.

In particular, in order to achieve optimum sample preparation and, primarily, the establishment of a state of phase equilibrium within the container 50, the device 10 is equipped with the already mentioned movement system 13 or the rotating and/or pivoting mechanism 13. The latter is actuated by an electromechanical actuator 13.1, which can, for example, be in the form of an electric motor. This can be a precise stepper motor. The rotating and/or pivoting mechanism 13 turns the bracket 12.2 and/or the receiving container 12 with the container 50 fixed thereon/therein and measuring head system 11 arranged on the receiving container 12. It is also conceivable that at least one light source 16 and/or an optical sensor 17 is arranged on the receiving container 12 and not connected in a stationary manner to the device 10, as shown by way of example in FIG. 1.

Additionally, in FIG. 1 an extraction unit 30 is shown which is known as a "Snift collector". The extraction device 30 is primarily arranged in an area of the receiving container 12 and/or the bracket 12.1 and can thus move together with these components or rotate about the axis of rotation 19. However, it is also conceivable for the extraction unit 30 to be arranged in a stationary manner inside or on the device 10, as optionally also indicated by the dashed line for better understanding in FIG. 1, and only connected via corresponding connecting elements to the receiving container 12 or the bracket 12.1. In both forms of embodiment a conduit element 31 for conveying, in particular, a gaseous medium from the extraction unit 30 extends from the extraction unit 30 to the piercing spike like 11.1, which, in particular, is pointed at its distal end which extends into the interior of the container 50. For the specific opening or closing of the conduit element a control valve 32 is arranged in the area of the conduit element 31. Via the spike 11.1, with the aid of the extraction unit 30, a gaseous medium, such as, for example air or also an air-carbon dioxide mixture can be removed, more particularly from the head room 50.3 of the container 50. This gaseous mixture can be conveyed to a container or also into the atmosphere. Advantageously the gaseous mixture is extracted before the start of sample measurement and preferably also before the start of a movement of the container 50 for mixing the media and establishing the state of phase equilibrium within the container 50, in order to be able to release air present in the container 50.

Figure 2:
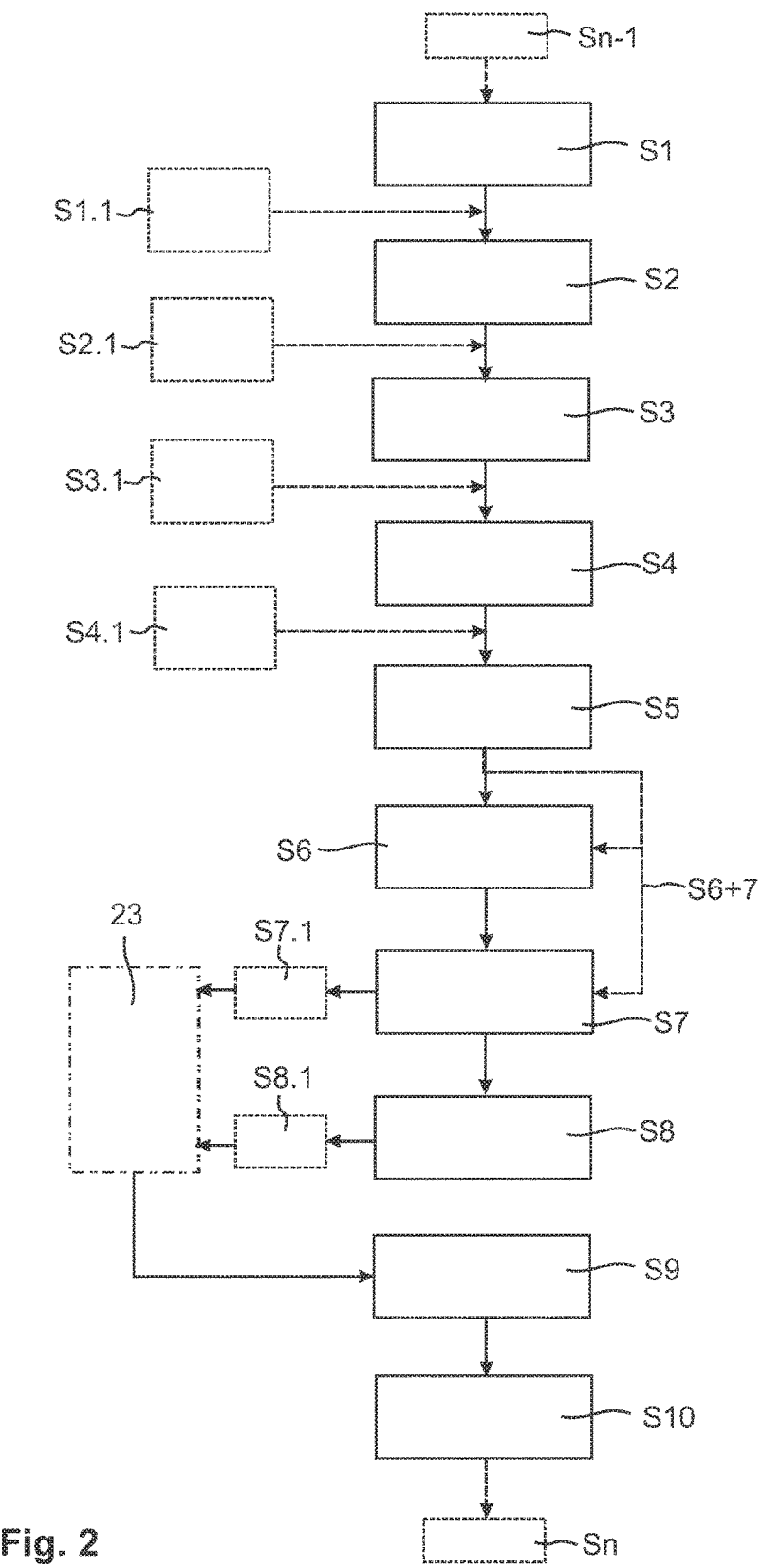

FIG. 2 schematically shows a possible course of the process in the examination of the sample and, in particular, for determining a physical, chemical and/or biological characteristic of a liquid or flowable medium. The process is primarily described by means of the determination of a value for the carbon dioxide present in the fluid medium 50.4 (cf. FIG. 1).

In a first stage S1 the container to be examined containing the liquid medium to be examined is arranged on a bracket or in a receiving container which is advantageously connected to the bracket. For the centring and alignment, in particular of the height of the container within the device, a container insert element based on the designed configuration of the container is selected. The selection of the container insert element can carried out manually by a person or also semi-automatically or fully-automatically by the device itself. For this, the device recognises, for example, the type and design of the container through reading in a code by way of a scanning unit. For this a person moves the scanning unit over the code, such as, for example, a bar code, QR code or similar (semi-automatic recognition) applied to the container itself or also to larger packaging or a container for packaging and transporting a batch of identical containers. However, it is also conceivable that, by means of a laser device for example, the device scans defined areas of a container to be introduced into the device, in order to thereby be able to identify the type of container (fully-automatic recognition). It is also possible that the device fully automatically scans a code of the container or that the laser unit can only scan defined areas of the container with the help of a person.

The selected container insert element is preferably arranged on a base area of the container and is advantageously inserted together with the container into the receiving container. The container insert element, which advantageously is made of a plastic-type material, is primarily resistant to heat, resistant to acids, simple in design and cost-effective to manufacture. For each form of container there is one container insert element, so that every conceivable form of container can be arranged in the device, more particularly in an area of the receiving container. The relevant container insert element is, in particular, selected in such a way that on arrangement in the receiving container the container projects between 5 mm and 7 mm beyond the edge of the receiving container. As a result of this, tight sealed closure of the measuring head arrangement with the receiving container and, in particular, the opening area of the container itself is possible, without, however, damaging the container, particularly in its opening area or in the area of the closing element.

Optionally it is possible that in a second step S2 the area of the container projecting from the receiving container, or the height of the projecting area, can be measured manually by a person, for example by way of a mechanical height gauge, or automatically by the device itself, for example by means of a light barrier, in order to identify a container projecting too little or too much from the receiving container and thus to be able to select another container insert element.

Thereafter, in a third step S3 the measuring head system with the spike arranged on it is placed on the receiving device, and in particular on the container. During this it is possible that the latter is translationally moved downwards along a movement path or that the container, preferably together with the receiving container and the bracket is translationally moved upwards to the stationary measuring head system. Preferably, however, the measuring head system is pivoted or tipped about a defined point of rotation or a defined axis of rotation until the piercing spike is arranged in a central area of the closure element and primarily in the area of a mid-point of the closure element and consequently is in contact with the closure element.

Optionally it is possible that in a further, fourth step S4 a section of a tension element, which is arranged, in particular, on an outer circumference of the receiving container, is now connected to a locking area of the measuring head system, and is, in particularly hooked into this. After hooking in the tension element it is now preferably manually operated by a person, wherein a lever arm of the tension element is turned or pressed down. Through this the tension element pulls the measuring head system further downwards in the direction of the container as a result of which the spike is also moved in the direction of the container and pierces the wall of the closure element. By means of a sealing element applied in the area of the closure element on the measuring head system, the closure element is advantageously encompassed in such a way that escaping of a gaseous as well as a liquid medium via the piercing site in the closure element out into the atmosphere or an area of the measuring head system is prevented.

If the device does not have a tension element, by means of a motor element, for example, the measuring head system is arranged on the container and the piercing spike moved through the closure element.

In a further step S5 the extraction device is activated which releases the air or a gaseous mixture consisting of air and carbon dioxide present in the container from the head room.

In a following sixth step S6 the container is preferably moved together with the measuring head system and the receiving container as well as the bracket and advantageously shaken or pivoted about an axis of rotation. During this pivoting or rotation the base area is at least at times positioned above the neck area of the container. The container is turned upside down. It is either fully rotated, namely about 360°, wherein the direction of rotation can alternate, i.e. change. However, it is also conceivable that the container is only turned about 180° in a first direction and then about 180° in a second direction which is opposite to the first direction back into the initial position. These directions of rotation can also alternate. Through this movement of the container carbon dioxide is released from the liquid medium.

In a seventh step S7 values relating to the pressure and the temperature of the media present in the container are measured. Through a shaking movement or also a rotating movement it is possible that the piercing spike, and therefore also a temperature sensor or also pressure sensor arranged in the piercing spike, contact first the liquid medium and then the gaseous medium. Consequently, depending on the rotation interval or the shaking interval and the corresponding measuring interval, the pressure and/or temperature first of the gaseous medium and then of the fluid medium can be measured or determined. It is thus conceivable that these media measurements are available in an alternating manner. In a step S7.1 the measurements are advantageously sent to a determination system 23 and, in particular, to an evaluation unit, which can be a component of the determination system 23 or also the measuring head system, and shown on a display unit.

Preferably an absolute pressure is measured which is shown together with a relative pressure in the display unit. The pressure can be indicated in bar or psi, while the temperature can be shown in ° Celsius or also in Fahrenheit.

Advantageously the measurement of temperature and pressure takes place continuously during the movement of the container, as shown through steps S6+7. Understood as "continuously" here is measurement at primarily even time intervals over a defined period of time, wherein the measurements can take place, for example, once or several times per second or once or several times per minute etc. The duration advantageously extends from, for example, a start of the process of moving the container until a state of equilibrium between the media present in the container is achieved.

If, in an eighth step S8 a state of equilibrium between the media present in the container is then determined, that is to say neither a change in temperature nor a change in pressure is determined over at least two, either consecutive measurements, or two measurements one or several measurements apart, the determination system 23 and, in particular, an evaluation unit, detects the presence of a state of phase equilibrium after transmission of the measurements in a step S8.1. The pressure and temperature values measured at the time of existence of a state of phase equilibrium are then used as the basic values for determining a value for the carbon dioxide present in a liquid medium.

For this, in a step S9 from the initial values the evaluation unit reads out a reference value correlating to the pressure and the temperature, namely the carbon dioxide content from a database or table of values preferably stored in a memory unit of the determination system. The correlating values were stored before the start of the measuring procedure for different liquid media, so that the evaluation unit can only refer to these stored values after recording the measurements. In a step S10 the read out carbon dioxide value is transmitted via a transmission and receiver unit of the determination system to the display unit and is displayed there.

It is also conceivable that a range, i.e. a spectrum of values, is shown, in which a carbon dioxide value in accordance with the available measurements for the corresponding liquid medium should be present so that the quality and also the taste of the medium, insofar as a foodstuff is involved, is assured. Advantageously the determined characteristic value is listed or shown within this range of values, so that it can simply read off whether the carbon dioxide content is, for example, in a borderline range and whether or not more carbon dioxide has to be added in the next production batch.

Before or after steps S1, S2, S3 and/or S4 it is possible that, for example, the type of medium present in the container, which is introduced into the device, is entered via a display unit by a person, such a laboratory assistant or a person involved in the manufacturing and/or filling of the medium, as shown through the steps Sn-1, S1.1, S2.1, S3.1, S4.1.

After determining a characteristic or a characteristic value of the liquid medium, the device, as shown by step Sn, is either manually or also automatically stopped, through which the movement and measuring procedure is discontinued. By loosening the tension element and opening or lifting off of the measuring head system the container can be removed from the device. As a result of the largely destructive examination due to, for example, the piercing of the closure element by the spike and/or the movement or shaking of the container and the diffusing out of the gaseous medium from the liquid medium, the container and liquid contained therein must be disposed of.

LIST OF REFERENCE NUMBERS

10 Device
10.1 Stationary base section/frame of 10
10.2 Slide contacts
10.3 Communication module
11 Measuring head system
11.1 Spike
11.2 Measuring unit/pressure measuring unit/temperature measuring unit
11.3 Communication module
11.4 Sealing element
12 Receiving container
12.1 Bracket
12.2 Container insert element
13 Direction of movement/rotary and pivoting movement device, -mechanism
13.1 Actuator
14 Evaluation unit
15 Display unit
16 Light source, in particular laser
17 Optical sensor for 16
18 Arrow for light beam
19 Arrow for direction of rotation
20 Memory unit
21 Transmission and receiving unit
22 Inputting unit
23 Determination system
30 Extraction device
31 Conduit element
32 Control valve
40 Tension element
50 Container
50.1 Closure element
50.2 Bottle
50.3 Head room
50.4 Liquid medium
50.5 Filling level
50.6 Neck area, space
50.7 Base area of the container 50
L Longitudinal axis of the container 50
Sn-1 Possible initial step: input of data
S1 First step: arranging the container in the device
S1.1 Possible intermediate step: input of data
S2 Second step: checking height
S2.1 Possible intermediate step: input of data
S3 Third step: arrangement of the measuring head system
S3.1 Possible intermediate step: input of data
S4 Fourth step: clamping in of the container
S4.1 Possible intermediate step: input of data
S5 Fifth step: activation of the extraction unit
S6 Sixth step: moving of the container
S7 Seventh step: measurement of pressure and temperature
S7.1 Intermediate step: transmission of measurements
S8 Eighth step: detection of a state of phase equilibrium
S8.1 Intermediate step: transmission of the date of the state of phase equilibrium
S9 Ninth step: reading out of a characteristic value
S10 Tenth step: displaying of the determined characteristic value
Sn Last step: removal of the container from the device

What is claimed is:

1. A device for determining at last one physical, chemical and/or biological characteristic of a liquid medium introduced into a sealable container comprising
a measuring head system with at least one pressure measuring unit for measuring a medium pressure of a gaseous medium and/or the liquid medium present in the container and a temperature measuring unit for measuring a medium temperature of the gaseous medium and/or the liquid medium,
a bracket at least for moving the container and
a determination system comprising memory which determines and stores a physical characteristic, a chemical characteristic and/or a biological characteristic of the liquid medium from at least one value relating to the measured medium pressure and the measured medium temperature;
wherein slide contacts are present between the measuring head system and a stationary base section of the device in order to allow data exchange via a lead.

2. The device in accordance with claim 1, wherein the measuring head system comprises a spike for piercing an area of a wall of the container and to introduce the temperature measuring unit and/or the pressure measuring unit into an interior area of the container.

3. The device according to claim 1, wherein the device comprises a receiving container for receiving at least a section of the container.

4. The device according to claim 1, wherein the measuring head system comprises at least one sealing ring for sealed closing of an opening of a receiving container and/or an opening of the container.

5. The device according to claim 1, wherein at least one clamp for locking the measuring head system in an area of an opening of a receiving container is arranged on a surface of an outer side of the receiving container.

6. The device according to claim 1, wherein the temperature measuring unit comprises a tubular insulation element made of a thermal energy-insulating material, through an interior of which a thermal energy conducting transmission element extends.

7. The device according to claim 1, wherein the determination system evaluates measured values comprising a member of a group consisting of: the medium pressure and the medium temperature, taking into consideration predefined correlation values.

8. The device according to claim 1, wherein for adjusting the height and centering the container, the device comprises a container insert element which can be arranged in the container.

9. The device according to claim 1, wherein at least one conduit element extracts a gaseous medium present in the container to an area of an outer side of a receiving container the at least one conduit element is connected to the spike.

10. The device according to claim 1, further comprising a communication module arranged in or on both the measuring head system and the base section of the device respectively in order to enable wireless data exchange to take place.

11. The device according to claim 1, wherein the slide contacts are electronic slide contacts transmitting electrical measuring signals while the bracket moves the container.

* * * * *